United States Patent [19]
Vallet Mas et al.

[11] Patent Number: 5,851,452
[45] Date of Patent: Dec. 22, 1998

[54] PROCESS FOR COATING DROPLETS OR NANOMETRIC PARTICLES

[75] Inventors: José Alberto Vallet Mas, Barcelona; Francisco Javier Galan Valdivia, Badalona; Nuria Carreras Perdiguer, Caldes de Montbui, all of Spain

[73] Assignee: Laboratorios Cusi, S.A., Barcelona, Spain

[21] Appl. No.: 586,731

[22] PCT Filed: Sep. 30, 1994

[86] PCT No.: PCT/ES94/00085

§ 371 Date: Jul. 20, 1996

§ 102(e) Date: Jul. 20, 1996

[87] PCT Pub. No.: WO95/31975

PCT Pub. Date: Nov. 30, 1995

[30] Foreign Application Priority Data

May 20, 1994 [ES] Spain ..................................... 9401121

[51] Int. Cl.[6] ...................................................... A61K 9/51
[52] U.S. Cl. ................. 264/4.6; 427/213.36; 427/213.3; 427/213.31; 427/213.32
[58] Field of Search ........................... 427/213.36, 213.3, 427/213.31, 213.32; 264/4.6

[56] References Cited

U.S. PATENT DOCUMENTS

| | | | |
|---|---|---|---|
| 4,761,255 | 8/1988 | Dahm et al. | 264/4.7 |
| 5,021,248 | 6/1991 | Stark et al. | 426/96 |
| 5,049,322 | 9/1991 | Devissaguet et al. | 264/4.1 |
| 5,118,528 | 6/1992 | Fessi et al. | 264/4.1 |
| 5,362,424 | 11/1994 | Lee et al. | 264/4.3 |
| 5,705,196 | 1/1998 | Valdivia et al. | 424/497 |

FOREIGN PATENT DOCUMENTS

| | | |
|---|---|---|
| 462003 | 12/1991 | European Pat. Off. . |
| 480729 | 4/1992 | European Pat. Off. . |
| 529711 | 3/1993 | European Pat. Off. . |
| 5567917 | 8/1993 | European Pat. Off. . |
| 2551072 | 3/1985 | France . |
| 2608988 | 7/1988 | France . |
| WO 93/25914 | 12/1993 | WIPO . |

OTHER PUBLICATIONS

Jarret et al. (1983) "Mechanism of bioderadation of poly-caprolactone". Polum Prep. (Am. Chem. Soc. div. Polum. Chem.) vol. 24, No. 1:32–3.

*Primary Examiner*—Jeffrey C. Mullis
*Attorney, Agent, or Firm*—Klauber & Jackson

[57] ABSTRACT

The process comprises: (1) preparing a fine dispersion of droplets or particles which contain, or are formed, of a chemical or biologically active substance in a phase comprised of a solvent and a non solvent of the polymer forming the coating and, optionally, a surfactant or suspending agent; (2) preparing a phase which contains the coat-forming polymer dissolved in a miscible solvent in any relationship with the prior dispersion, (3) mixing both phases continuously while maintaining constant the relationship between the phases and the mixture volume, and simultaneously spraying the resultant mixture in an evaporation system with temperature and vacuum conditions which provide for the instantaneous evaporation of the solvent from the polymer, causing the deposition of the polymer around the particles or droplets. Applications to pharmacy, medicine, cosmetics, veterinary, chemical industry, agriculture are discussed.

15 Claims, 2 Drawing Sheets

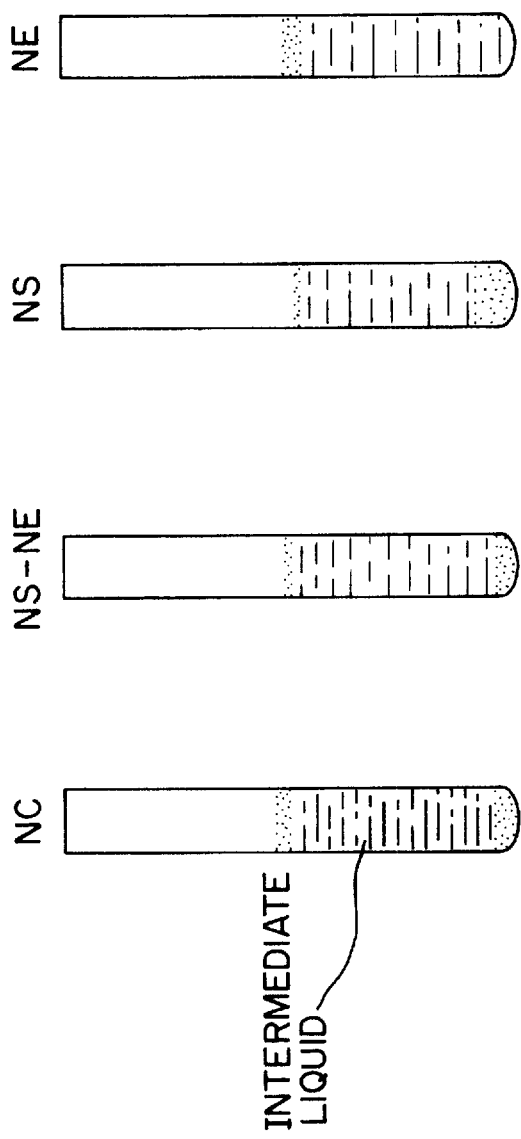

PROCESS FOR COATING DROPLETS OR NANOMETRIC PARTICLES

TECHNICAL FIELD OF THE INVENTION

The present invention is comprised within the technical field of microencapsulation, particularly, in the coating of droplets of particles with sizes comprised within the nanometric range, using biodegradable and bio-compatible polymers of different nature. The thus obtained products have important applications in pharmacy, medicine, cosmetics, veterinary, chemical industry, agriculture etc.

BACKGROUND OF THE ART

The obtention of a fine suspension of particles formed by a biodegradable polymer, polycaprolactone, by means of precipitation due to a change of solvent, has been described in the scientific work "Mechanism of the biodegradable of polycaprolactone" (1983), Jarret, P. et al. Polym Prep. (Am. Chem. Soc. Div. Polym. Chem.) Vol. 24 No. 1, page 32–33.

EP Patent 0274961B1 (which corresponds to U.S. Pat. No. 5,049,322) describes a method for the obtention of vesicular type, spherical particles having a size less than 500 nm. The method comprises the preparation of a phase containing a polymer, an oil and a substance to be encapsulated in a solution or dispersion. The phase is added, under agitation, to another phase formed by a non solvent of the polymer and of the oil, producing the precipitation of the polymer and subsequently the removal of the solvents by lyophilization. On incorporation of one phase over another, the size of the reactor which contains the mixture is increased depending on the final volume desired. This implies the necessity of a scaling to adapt the manufacturing conditions. There exists the difficulty in large volumes in that, once the mixture is formed, the polymer solvent must be in contact with the nanocapsules for a long period, with the possibility of producing the re-dissolution of the same, or the extraction of the active substance to the external phase. On the other hand, the removal of solvents by means of lyophilization is a slow and expensive process, with the additional disadvantage that when inflammable solvents are involved, it is highly dangerous.

The present invention relates to the coating of already formed droplets or particles, so that it is not necessary to agitate the mixture, which is effected by incorporation of the two phases in a device in which the mixture flows continuously, with the immediate production of the evaporation of the solvents. The elaboration and facility conditions (reaction volume) is always the same, independent of the final volume to be obtained, so that it does not require scaling for the obtention of industrial quantities. The solvent remains in contact with the recently coated vesicules during a very short period, so that the re-dissolution of the coating and the possible extraction of the active principle to the external phase is avoided, whatever the volume to be prepared.

The process described in FR A2 515960 allows the obtention of poly alkyl-cyanoacrylate biodegradable nanocapsules, which separate from the polymerization of the corresponding monomer. These nanocapsules contain a biologically active substance. The disadvantage of this method is that it requires a polymerization stage, so that it can only be used with specific polymers. Besides this important limitation, it involves the difficulty of controlling the polymerization and the possible existence of residual monomers which may, in some cases, be toxic. The present invention has the advantage that it does not require a polymerization, being a more rapid process and being applicable to a great number of polymers of diverse nature.

The process described in EP 0480 729 A1 consists of the coating of droplets in oil, containing active principles for oral administration, with a polysaccharide with chelator capacity (sodium alginate) which hardens on the addition of multivalent cations, resulting in micro-capsules with sizes over 1 $\mu$m. Finally, it is lyophilized to obtain a product in powder form. This method is limited to the employment of polysaccharides with chelator capacity. Likewise, sonication is necessary, not being applicable for those active substances which are degraded by ultrasonic action. Additionally, the use of a multivalent cation solution makes difficult its employment in any form other than oral. The present invention provides coated droplets with sizes appreciably below 1 $\mu$m, does not require hardening agents, does not use sonication, and the product obtained may be administered orally, parenterally, or through the nose, eyes, skin, lungs or any other form of administration.

In the process described in EP 0462003 A1, microcapsules, with sizes between 25 and 100 $\mu$m with oil inside, are obtained when dried by atomization and oil/water emulsion formed by the active principle and a gastroresistant polymer aqueous solution, producing a fine powder, by means of the use of an atomizer at a temperature of 140° C. The use of high temperatures is a disadvantage since it limits the use of this method when the encapsulated substance is thermosensitive. This method is only usable for water-soluble polymers, and additionally differs from the object of the present invention in that the sizes obtained are much greater.

The process described in EP 0556917 A1 allows the obtention of biodegradable microcapsules containing an active substance separating from the ultrasonic atomization of a solution or suspension, over a non solvent, in such a way that the coagulated droplets are transferred to a second non solvent. This method, besides being complicated and requiring various solvents and a special atomizer by sonication, results in microcapsules with sizes over 10 $\mu$m.

Unlike all previously mentioned patents, the present invention is a method which allows the obtention of large quantities of the product without changing the conditions or facilities, and consequently, is easily industrialized. This method allows the rapid and continuous coating of temperature or sonication-sensitive active substances, resulting in a final product which is usable in any field, and especially in the pharmacy and veterinary field.

DESCRIPTION OF THE INVENTION

The present invention concerns to a new process for the coating of droplets or particles with sizes below a micrometer, which contain, or are formed, of one or various chemical or biologically active substances. Consequentially, the present invention allows the obtention of particles or droplets coated by one or various biodegradable and/or bio-compatible polymers with diameters comprised within 100 and 100 nm, preferably within 200 and 500 nm.

For the performance of the present invention, a fine dispersion of droplets or particles is prepared. When dealing with droplets, the active substance is dissolved in a lipidic substance (generally an oil) or in a substance at fusion point below the temperature of the dispersing means. The droplets may also be consist of the actual active substance. When dealing with solid particles, these may be the actual active substance or have the active substance dispersed inside. They may also be part of a microorganism or integral microorganisms with sizes below one micrometer. The dispersing phase is constituted by a solvent and a non solvent of the polymer which forms the coating and, optionally, contains one or more surfactant or suspending agents (PHASE 1). The relationship between the solvent and the non solvent in PHASE 1 must be the adequate one, so that the coat-forming polymer does not precipitate when mixed with the phase which contains the polymer. The phase which contains the coat-forming polymer (PHASE 2) is prepared by dissolving the coat-forming polymer in a solvent equal to the one used as part of PHASE 1, or any other which is miscible in a high relationship with the solvent of the polymer used in PHASE 1.

Once PHASE 1 and PHASE 2 have been separately prepared, they are lead through separate tubes to a mixing zone, where they continuously contact without agitation or ultra-sonication, keeping their relationship constant (which avoids the instantaneous precipitation of the polymer) and the volume of the mixture. During the mixing, the polymer does not deposit on the droplets or particles, though the deposition process may be initiated, which occurs instantaneously when the mixture is pulverized in an evaporation system with temperature and vacuum conditions allowing the rapid evaporation of the polymer solvent, which provides for the immediate deposition of the polymer around the droplets or particles. Optionally, part of the non solvent, or the totality of the same, may be eliminated until a concentrated or dry product is obtained.

The conduction of the phases towards the mixture device zone, may be carried out be means of any pumping system, or with the help of pressure or vacuum.

It is a characteristic of this process that, once PHASE 1 and PHASE 2 have been prepared, the formation of the mixture, the pulverization of the mixture and the deposition of the polymer are carried out in a totally continuous and simultaneous manner in time.

The relation between the solvent and the non solvent of the coat-forming polymer in the initial dispersion must be adequate so that when in contact with the phase which contains the polymer in the solution, the immediate deposition of the polymer tends to precipitate in the mixture of the phases, the small dimensions of the mixing zone allows the entrance of the phases in the mixing zone, and their exit in the form of powder through the other end is so rapid that the polymer has no time to precipitate. In this way, an uncontrolled precipitation is avoided which would produce the formation of aggregates, and it ensures that the coating is produced at the amount of pulverization or nebulization.

The selection of the solvent and the non solvent of the polymer in the initial dispersion is carried out depending on the chemical and physicochemical characteristics of the polymer, or the oil or lipidic substance, and of the active substance to be incorporated.

If the coat-formed polymer is non soluble in water, the non solvent may be a more or less complex aqueous solution, and the solvent may be any organic solvent which is miscible with a high relationship in water, capable of dissolving the polymer. The solvent of the polymer may be for instance, an alcohol such as ethanol, methanol, isopropanol, a ketone of low molecular weight such as acetone or methyl ethyl ketone or any other solvent such as acetonitrile or tetrahydrofuran. Normally, the solvent of the polymer has a dielectric constant over 15.

In the case that the polymer is soluble in an organic solvent and water soluble depending on the pH or temperature, the aqueous solution of the initial dispersion must be adjusted to a pH and/or temperature at which said polymer is insoluble to ensure the deposition of the polymer when the solvent is evaporated during the pulverization.

The lipidic substance to be dispersed in the water may be a natural oil such as coconut oil, soya oil, olive oil, castor-oil, a mixture of capric acid tristearates and capric acid with glycerol, a mixture of saturated and unsaturated acid fats $C_{12}$–$C_{18}$ where the main constituent is the linolenic acid (48%), a mixture of unsaturated poly-glycosided glycols consisting of glycerols and polyethylene glycol esters, a mixture of saturated poly-glycosided $C_8$–$C_{10}$ glycerols, a palmitate ester of glycerol formed by mono, di and triglycerols of natural $C_{16}$ and $C_{18}$ fatty acids, or a mixture of the same, a mineral oil or a phospholipid.

Generally, the concentration of the lipidic substance in the final product is comprised within 0.1 and 10% (w/V), preferably within 0.5 and 5% (w/V).

The surfactant or emulgent agent of PHASE 1 may be amphoteric such as soya or egg lecithin, anionic such as sodium laurysulfate, cationic such as benzalkonium chloride or non ionic such as sorbitan monoleate, sorbitan monestearate, a polysorbate or a copolymer of polyoxyethylene-polyoxypropylene or a mixture of the same.

The suspending agent may be a dextran, poly-vinylic alcohol, a cellulosic derivative, or a natural rubber such as xanthene rubber. Any of these may be used in combination with a surfactant agent enumerated above.

The surfactant or suspending agent concentration in the final formula is comprised between 0.01 and 10% (w/V).

In PHASE 2, the polymer used may be a synthetic polymer such as the glycols derived from propiolactone, butyrolactone and the epsilocaprolactone; a hemisynthetic polymer such as cellulose acetobutyrate, ethylcellulose, hydroxpropylmethylcellulose acetophtalate; the acrylic acid copolymers and the acrylic polymer, lactic acid copolymers with the glycol acid or the polycaprolactone. Other polymers which may be employed are the cellulose acetophtalate, the polyanhydrides, the polyalphahydroxy-acids and the natural polymers.

The concentration of the coat-forming polymer in the organic phase is comprised between 0.01 and 5% (w/V).

Different forms of mixing the two phases exist. It may be performed through two parallel tubes, producing the union in a concentric or "Y" shaped zone, in such a way that the two phases are joined simultaneously. The volumes of the phases may be equal or the volume of one phase may be greater with respect to the other. The mixing zone has, on the extreme end at which the phases are incorporated, a suitable device, so that the mixture exists in powder form towards an evaporation system in which the solvent of the polymer is totally eliminated and, optionally, part of, or the whole of, the non solvent under reduced pressure and at a temperature below 50° C. The degree of vacuum and the temperature must be adjusted depending on the solvent and the immediate deposition of the polymer around the droplets or particles is ensured, and the formation of aggregates or the appearance of uncoated particles is avoided.

The product thus obtained may be used in suspension or dry powder form, be extruded, compressed or granulated and be used alone or as part of a more complex blend.

An analysis has been made of the experimental results obtained in some specific tests performed according to the process of the present invention.

1. Nanoemulsion coating tests without drugs

In order to study the suitability of the process for coating droplets, which is the object of the present invention, various formulations were prepared with the purpose of checking that the polymer is mainly deposited around the oil droplets instead of individually precipitating in the form of nanospheres, the greater part of the oil droplets remaining uncoated. For this, the three types of products which could be formed were separately prepared: nanocapsules, nanoemulsions and nanospheres.

a) A nanoemulsion of a mixture of caprylic acid and caprynic acid triesters with polyepsiloncaprolactone-coated glycol, was prepared according to the process specified in the description of the present invention.

b) A nanoemulsion mixture of the caprylic acid and caprynic acid triester with glycol was prepared in the same manner as in the previous section (a), but without adding polymer in the organic solution (PHASE 2) of the description of the present invention.

c) For the obtention of nanospheres, the process detailed in the description of the present invention was followed, but using only the mixture of solvents and non solvents of the coat-forming polymer (polyepsiloncaprolactone), without oil, as PHASE 1.

A determination was made of the particle size, the polydispersity and the Z potential of the resultant products of (a), (b) and (c) with the Zetasizer 3 (Malvern Instruments England).

As is shown in Table 1, the values of the average size and the polydispersity of the uncoated oil droplets are greater than those of the coated oil droplets, and these, in turn, are greater than the nanosphere.

The Z potential (parameter which indicates of the electric load on the surface of the droplets and particles), is −18 mV for coated droplets, while for the free oil droplets, it is −8 mV and for the nanosphere it is −14 mV.

TABLE I

|    | Non ionic Surfactant final % (w/V) | Poly caprolactone final % (w/V) | Oil Final % (w/V) | Average size (nm) | Poly-dispersity | Z potential (mV) |
|----|------|------|------|-----|-------|-----|
| NC | 2.5  | 1.25 | 2.5  | 192 | 0.150 | −18 |
| NE | 2.5  | —    | 2.5  | 307 | 0.302 | −8  |
| NS | 2.5  | 1.25 | —    | 149 | 0.022 | −14 |

NC: coated nanoemulsion;
NE: nanoemulsion;
NS: nanospheres.

The values of size, polydispersity and Z potential correspond to the average of 10 measurements.

An evaluation was conducted, by means of electronic microscopy, at transmission of 66,000 magnification on diverse samples of the resultant products of (a) and (b) which were previously tinted with uranyl acetate at 1%.

As can be observed in FIG. 1, the uncoated oil droplets (A), appear as uniform particles which adapt with one another, while coated oil droplets (B) appear as particles with a less dense core, surrounded by a transparent zone limited by a dark edge (polymeric coating).

2. Nanoemulsion coating test with drug

The proceedings were similar to the previous section for the formulations without active principle, and a mixture of nanoemulsion and nanosphere was additionally prepared.

a) A nanoemulsion of a mixture of caprylic acid and caprynic acid triesters was prepared with polycaprolactone-coated glycol, containing indomethacin at 0.1% (w/V) according to the process detailed in the description of the present invention.

b) A nanoemulsion of a mixture of caprylic acid and caprynic acid triesters was prepared with glycol containing indomethacin at 0.1% (w/V) in the same manner as in previous section (a) but without adding polyepsiloncaprolactone of the present invention.

c) For the obtention of indomethacin nanospheres at 0.1% (w/V), the process detailed in the description of the present invention was followed, but using only a mixture of solvent and non solvent of the coat-forming polymer (polyepsiloncaprolactone), without oil, as in PHASE 1, Additionally, a dispersion of oil droplets, and nanoparticles was prepared, mixing at equal parts, the resultant products of previous sections (b) and (c).

A determination was made of the size of the particle, the polydispersity and the Z potential with a Zetasizer 3 (Malvern Instruments, England), and 5 ml of each one of the products was centrifuged during 2 cycles of 1 h at 4000 rpm in a centrifugal Selecta model Centromix.

The results are represented in Table II and in FIG. 2. As may be observed in Table II, the average size values and the polydispersity values of the uncoated oil droplets are greater than those of the coated oil droplets and these, in turn, are greater than those of the nanospheres. The average size and the polydispersity of the nanosphere mixture and the uncoated oil droplets give intermediate values to those corresponding to the separate products and greater than those obtained for the coated droplets. Likewise, the nanosphere and nanoemulsion mixture showed a bimodal distribution (two populations of particle sizes). As regards to the Z potential, the values obtained for the mixture of the nanospheres and the uncoated oil droplets are within the values corresponding to each product separately.

The Z potential of the coated droplets is greater (in absolute values) than those of the nanospheres, the uncoated droplets and their mixture. Consequently, the product obtained by the process of the present invention is not the result of a mixture of precipitated polymer particles (nanospheres) and of uncoated oil droplets.

TABLE II

|         | Non-ionic surfactant final % | Poly caprolactone final % (w/V) | Oil final % (w/V) | Indo-metacine final % (p/V) | Average size (nm) | Poli-dis. | Pot. (mV) |
|---------|------|------|------|-----|------|-------|-----|
| NC      | 2.5  | 1.25 | 2.5  | 0.1 | 419  | 0.157 | −38 |
| NE      | 2.5  | —    | 2.5  | 0.1 | 1026 | 0.319 | −24 |
| NS      | 2.5  | 1.25 | —    | 0.1 | 345  | 0.121 | −36 |
| NS + NE | 2.5  | 1.25 | 2.5  | 0.1 | 511  | 0.199 | −31 |

NC: coated nanoemulsion;
NE: nanoemulsion;
NS: nanospheres;
NS + NE: mixture at equal parts of nanospheres and nanoemulsions.

The values of size, polydispersity and Z potential correspond to the average of 10 measurements.

As may be observed in FIG. 2, the nanospheres (NS) show a white sediment at the bottom of the tube, while the nanoemulsion (NE) shows a whitish float. The nanosphere and nanoemulsion mixture (NS+NE) presents both a sediment and a floating, as well as a practically transparent intermediate liquid. On the other hand, the coated oil droplets (NC) show a minimum sediment and floating but the intermediate liquid is much cloudier (whitish). This intermediate coat, which is wider and cloudier, corresponds to the coated oil droplets with an intermediate density between that of the oil droplets (less dense) and that of the nanospheres (denser).

BRIEF DESCRIPTION OF THE FIGURES

FIG. 2 shows a comparison of the appearance of the intermediate liquid in test 2, between the nanospheres (NS), the nanoemulsion (NE), the mixture of nanospheres and nanoemulsion (NS+NE) and the coated oil droplets (NC).

EXAMPLES OF THE INVENTION

Figure 1A:
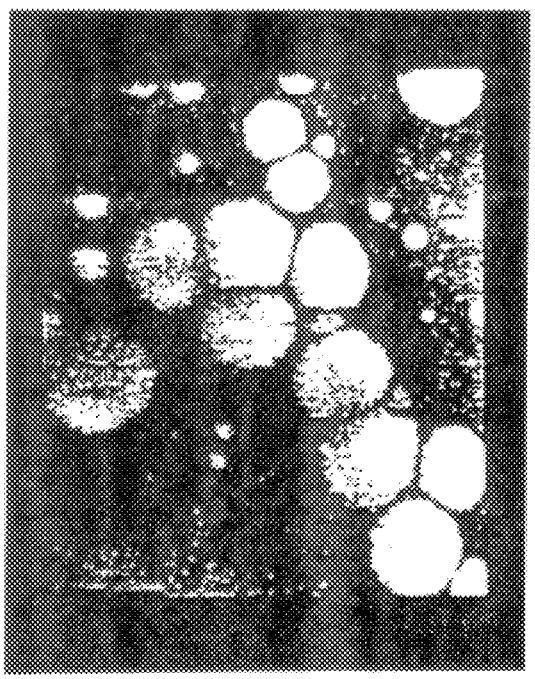
In FIG. 1:(A) represents uncoated oil droplets which appear as uniform particles which adapt with one another; and 1(B) represents the coated oil droplets which appear as particles with a denser core, surrounded by a transparent zone limited by a dark edge (polymeric coat).
Figure 1B:
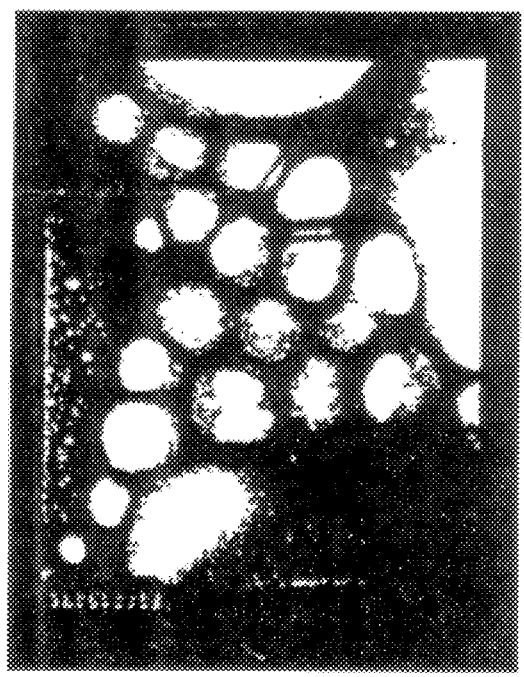

The present invention is additionally illustrated by means of the following examples, which must not be considered as limiting the scope of the same, and which is defined by the attached note of the claims:

For the description of the examples, the commercial names of the products are used, which must be understood to be any product with the same characteristics, commercialized by any other company. The products are as follows:

Miglyol 812® (Dynamit Nobel, Sweden): is a mixture of caprylic acid triesters and caprynic acid with glycol.

Commercial linolenic acid (Henkel, Dusseldorf): is a mixture of saturated and unsaturated fatty acids $C_{12}$–$C_{18}$ where the main constituent is linolenic acid (48%).

Eudragit L 12 5 (Rohm Pharma, Darmstadt): is a polymerized anionic of methacrylic acid and methyl methacrylate.

Lutrol F68 (BASF, Germany): is Poloxamer 188 which is a copolymer of polyoxyethylene and polyoxypropylene.

EXAMPLE 1

Nanoemulsion of Miglyol 812® Coated With Polyepsilon Caprolactone 0.625 g of Lutrol F 68® is dissolved, under agitation, in 62 ml of deionized water and filtered through 0.22 μm. 0.625 g of Miglyol 812® dissolved in 62 ml of acetone. The acetonic solution is incorporated to the initial acqeous solution under magnetic agitation, so that a dispersion of droplets with average size below 1 μm is obtained (PHASE 1), 0.312 g of polyepsiloncaprolactone is dissolved in 125 ml of acetone with the help of ultrasonication (PHASE 2). The two phases are continuously mixed through the two parallel tubes, maintaining the relation of the phase constant in the mixing zone and pulverizing the resultant mixture towards the evaporation system simultaneously to the formation of the mixture. The evaporation system removes under reduced pressure and at a maximum temperature of 45° C., the acetone (polymer solvent) so that the deposition of the polymer around the oil droplets is produced and part of the water (non-solvent of the polymer) is eliminated until a final volume of 25 ml is reached. The average size of the coated droplets, measured in a Zetasizer 3 (Malvern Instruments, England) was 192±0.1 nm.

EXAMPLE 2

Nanoemulsion of Miglyol 812® Coated With Polyepsiloncaprolactone

Follow the technique described in Example 1, but the ratio of solvents in the initial dispersion is of 2:3 water/acetone expressed in volumes, instead of 1:1 water/acetone. The average size of the coated droplets, measured in a Zetasizer 3 (Malvern Instruments, England) was 307±0.5 nm.

EXAMPLE 3

Nanoemulsion of Miglyon 812® Coated With Polylacticglycolic Copolymer 75:25

The technique described in Example 1 is followed, but using 0.830 g of Lutrol F68®, 0.207 g of polylactic-glycolic copolymer instead of polyepsiloncaprolactone and 0.415 g of Miglyol 812®. The average size of the coated droplets, measured in a Zetasizer 3 (Malvern Instruments, England) was 197±5 nm.

EXAMPLE 4

Nanoemulsion of Carteolol Base at 0.2% Coated With Polyepsiloncaprolactone 0.375 g Lutrol F68® was dissolved in 40 ml of deionized water and filtered through 0.22 μm under agitation. 0.030 g of carteolol base was dissolved in 0.375 g of commercial linolenic acid, and the resultant solution is added to 60 ml of acetone. The acetonic solution was incorporated into the initial aqueous solution under magnetic agitation to obtain a dispersion of droplets with average size below 1 μm (PHASE 1). 0.187 g of polyepsiloncaprolactone was dissolved in 100 ml of acetone with the help of ultrasonication (PHASE 2). The two phases were continuously mixed through two parallel tubes, while maintaining the ratio of the phases constant in the mixing zone, and pulverizing the resultant mixture the evaporation system simultaneously with the formation of the mixture. Using an evaporation system, the acetone was removed (solvent of the polymer), under reduced pressure and at a maximum temperature of 45° C., so that the deposition of the polymer around the oil droplets was produced and part of the water was removed (non-solvent of the polymer) until a final volume of 25 ml is reached. The average size of the coated droplets, measured in a Zetasizer 3 (Malvern Instruments, England) was 375±3 nm.

For separating the coated droplets of the external aqueous phase, the ultrafiltering-centrifugal technique was used, determining, by means of HPLC, the concentration of carteolol in the total formula and in the filtration. The percentage of the encapsulation of the carteolol was calculated by the difference between the concentration in the total formula and that of the filtration. The percentage of encapsulation was of 70%

EXAMPLE 5

Nanoemulsion of Indomethacin at 0.1% Coated With Polyepsiloncaprolactone 1.66 g of Lutrol F68® was dissolved in 100 ml of deionized water and filtered through 0.22 μm under agitation, 0.050 g of indomethacin was dissolved in 0.83 g of Miglyol 812® with the application of heat, and the resultant solution added to 100 ml of acetone. The acetonic solution was incorporated into the initial aqueous solution under magnetic agitation, so as to obtain a dispersion of droplets with average size below 1 μm (PHASE 1), and 0.415 g of polyepsiloncaprolactone was dissolved in 200 ml of acetone with the help of ultrasonication (PHASE 2). The two phases were mixed continuously through the two parallel tubes, maintaining the ratio of the phases constant in the mixing zone and pulverizing the resultant mixture towards the evaporation system simultaneously with the formation of the mixture. Using an evaporation system, the acetone was removed (solvent of the polymer), under reduced pressure and at a maximum temperature of 45° C., so that the deposition of the polymer around the oil droplets was produced and part of the water was removed (non solvent of the polymer) until a final volume of 50 ml was reached. The final pH was adjusted to 5.5 with HCl 0.1M. The average size of the coated droplets, measured in a Zetasizer 3 (Malvern Instruments) was 551±15 nm.

For the separation of the coated droplets of the external aqueous phase, the ultrafiltering-centrigal technique was used, determining by means of HPLC, the concentration of indomethacin in the total formula and in the filtration. The percentage of encapsulation of the indomethacin was calculated by the difference between the concentration in the total formula and that of the filtrate. The percentage of encapsulation was 99%

EXAMPLE 6

Nanoemulsion of Miglyol 840® Coated With Eudragit 12.5 p®

0.375 G of Lutrol F68° was dissolved, under agitation in 40 ml of deionized water and filtered through 0.22 µm. The pH was adjusted to 4.5 with HC 0.1M. 0.37 g of Miglyol 840® was dissolved in 60 ml of acetone. The acetonic solution was incorporated into the acetone. The acetone solution was incorporated into the initial aqueous solution under magnetic agitation, so that a dispersion of droplets with average size below 1 µm was obtained. (Phase 1). 0.150 g of Eudragit L 12.5 p® was dissolved in 100 ml of acetone (Phase 2). The two phases were continuously mixed through the two parallel tubes constantly maintaining the ratio of phases in the mixing zone and pulverizing the resultant mixture towards the evaporation system simultaneously with the formation of the mixture. Using an evaporation system, the acetone (solvent of the polymer) was removed under reduced pressure and at a maximum temperature of 45° C., so that the deposition of the polymer around the oil droplets was produced and part of the water (non solvent of the polymer) was removed until a final volume of 15 ml is reached. The average size of the coated droplets, measured in a Zetasizer 3 (Malvern Instruments) was of 832±nm.

EXAMPLE 7

Nanoemulsion of Carteolol at 0.1% Coated With Eudragit L 12.5 P®

The technique described in Example 6 was followed, but substituting the Miglyol 840® commercial linolenic acid for the Miglyol 840®, and 0.030 g of carteolol base was included in the oil. The average size of the coated droplets measured in a Zetasizer 3 (Malvern Instruments) was of 290±12 nm.

For the separation of the coated droplets of the external aqueous phase, the ultra-filtering-centrifugal technique was used, determining, by means of HPLC, the carteolol concentration in the total formula and in the filtration. The percentage of encapsulation of the carteolol was calculated by the difference between the concentration in the total formula and that of the filtration. The percentage of encapsulation was 66%.

EXAMPLE 8

Polystyrene Latex Coated With Polyepsiloncaprolactone 0.125 g of Lutrol F68® was dissolved, under agitation, in 40 ml of deionized water and filtered through 0.22 µm. To this solution was added 100 µm of polystyrene latex with an average particle size of 200 nm and a Z potential of −30.81 mV measured in a Zetasizer 3 (Malvern Instruments) and subsequently 20 ml of acetone was added, to obtain a dispersion of droplets with average size below 1 µm (Phase 1). 0.01 g of polyepsiloncaprolactone was dissolved, by means of ultra-sonication in 25 ml of acetone (Phase 2). The two phases were continuously mixed through the two parallel tubes, maintaining the relationship of the phases constant in the mixing zone and pulverized the resultant mixture towards the evaporation system simultaneously with the formation of the mixture. Using an evaporation system, the acetone (solvent of the polymer) was removed under reduced pressure and at a maximum temperature of 45° C., in order to produce the deposition of the polymer around the latex particles and part of the water (not the solvent of the polymer) was removed until a final volume of 7 ml is reached. The average Z potential of the coated droplets, measured in a Zetasizer 3 (Malvern Instruments) was 28 6±1.5 mV.

EXAMPLE 9

Polystrene Latex Coated With Eudragit I 12.5 p

The same procedure for Example 8 is followed, but replacing the polyepsiloncaprolaotone with Eudragit L 12.5 P. The initial solution of water and Lutrol F68 was adjusted to approximately pH4. The average size of the coated droplets, measured in a Zetasizer 3 (Malvern Instruments), was 270±12 nm and the Z potential of 17.39±1.5 mV.

We claim:

1. A process for coating droplets or solid particles with sizes below 1 micron which contain a chemically or biologically active substance in which the coating is comprised of one or more biocompatible polymers, characterized by;

preparing a first phase comprising a fine dispersion of droplets or solid particles in a solution of a solvent and a non solvent for the polymer forming the coating and containing a surfactant or suspending agent, preparing a second phase which contains the polymer or mixture of polymers dissolved in a solvent or mixture of miscible solvents, mixing the two phases continuously in a mixing zone without agitation or ultrasonication while maintaining a constant ratio of the two phases and a constant volume of the two phases in the mixing zone, and spraying the resulting mixture into an evaporation system where it is converted into a pulverized form by elimination of the solvent under reduced pressure so that the polymer is deposited around the droplets or particles.

2. A process according to claim 1 wherein the average diameter of the coated particles or droplets is below 1 µm.

3. A process according to claim 1 or 2 wherein the polymer forming the coating is biodegradable and/or biocompatible.

4. A process according to claim 1 or 2 wherein the active substance is a drug or a cosmetic substance.

5. A process according to claim 1 or 2 wherein the active substance is a biologically active product, a microorganism or fragments of microorganisms.

6. A process according to claim 1 or 2 wherein the active substance is dissolved or dispersed in the droplets or particles.

7. A process according to claim 1 or 2 wherein the droplets or particles contain the active substance.

8. A process according to claim 1 or 2 wherein the droplets contain an oil or lipidic substance.

9. A process according to claim 1 or 2 wherein the mixing, pulverization and the deposition of the polymer is carried out continuously and simultaneously in time.

10. A process according to claim 1 or 2 wherein the proportions of the solvent and the non-solvent of the polymer in the first phase allows the mixing of phases without producing the instantaneous deposition of the polymer.

11. A process according to claim 1 or 2 wherein the concentration of the surfactant agent comprises 0.01 % to 10% (w/V).

12. A process according to claim 1 or 2 wherein the concentration of the suspending agent is between 0.1% and 10% (w/V).

13. A process according to claim 1 or 2 wherein the solvents of the polymer forming the coating have a dielectric constant over 15.

14. A process according to claim 1 or 2 wherein the concentration of the polymer forming the coating is between 0.01% and 10% (w/V).

15. A process according to claim 1 or 2 wherein the final product is lyophilized, extruded or compressed.

* * * * *